United States Patent [19]

Arai et al.

[11] Patent Number: 4,659,850

[45] Date of Patent: Apr. 21, 1987

[54] POLYORGANO(HYDRO)SILAZANE AND PROCESS FOR PRODUCING SAME

[75] Inventors: Mikiro Arai, Saitama; Takeshi Isoda, Niiza; Osamu Funayama, Saitama, Japan

[73] Assignee: Toa Nenryo Kogyo Kabushiki Kaisha, Tokyo, Japan

[21] Appl. No.: 849,755

[22] Filed: Apr. 9, 1986

[30] Foreign Application Priority Data

Dec. 28, 1985 [JP] Japan .................... 60-293472

[51] Int. Cl.$^4$ ............................................. C07F 7/10
[52] U.S. Cl. .................... 556/409; 556/412; 528/12; 528/19; 528/21; 528/23; 528/28; 528/38
[58] Field of Search ............... 556/409, 412; 528/12, 528/19, 21, 23, 28, 38

[56] References Cited

U.S. PATENT DOCUMENTS

| | | | |
|---|---|---|---|
| 3,318,823 | 5/1967 | Aylett et al. | 556/409 X |
| 4,340,619 | 7/1982 | Gaul | 528/38 X |
| 4,482,669 | 11/1984 | Seyferth et al. | 528/28 X |
| 4,482,689 | 11/1984 | Haluska | 528/38 X |
| 4,540,803 | 9/1985 | Cannady | 556/412 |
| 4,595,775 | 6/1986 | Arkles | 556/409 |

Primary Examiner—Paul F. Shaver
Attorney, Agent, or Firm—Michael N. Meller

[57] ABSTRACT

A novel polyorgano(hydro)silazane having the compositional formula: $(RSiHNH)_x[(RSiH)_{1.5}N]_{1-x}$, wherein R is an alkyl group, an alkenyl group, a cycloalkyl group, an aryl group, another group in which the atom directly bound to Si is carbon, an alkylsilyl group, an alkylamino group, or an alkoxy group, and $0.4 < x < 1$. This polyorgano(hydro)silazane is produced by reacting a complex of organo(hydro)diholosilane and a base with dry ammonia. This novel silazane is useful as a ceramic starting material, a polymer hardening agent, a densifying agent, a surface coating material, etc., and can be produced safely and at a low cost.

19 Claims, 4 Drawing Figures

POLYORGANO(HYDRO)SILAZANE AND PROCESS FOR PRODUCING SAME

BACKGROUND OF THE INVENTION

1. Field of the Invention

This invention relates to a novel polyorgano(hydro)-silazane, which is useful as a ceramic starting material, a polymer hardening agent, a densifying agent, a surface coating agent, etc., and can be produced according to a process having a lower cost and a superior stability to that of polyorgano(hydro)silazanes of the prior art. The present invention also relates to a process for producing such a novel polyorgano(hydro)silazane.

2. Description of the Related Art

Known in the art are polyorgano(hydro)silazanes which are produced by allowing organodichlorosilanes such as methyldichlorosilane to react with dry ammonia in a non-reactive solvent. The polyorgano(hydro)silazanes produced by this method have a composition represented by $-\text{RSiHNH})_n$ [wherein R is an organo group such as an alkyl group, aryl group, etc., and n represents a polymerization degree], but the polymerization degree n thereof is low and the composition comprises a mixture of cyclic compounds with $n = 3$ to 5.

It has been proposed to produce a polysilazane with a high molecular weight by using such a cyclic product with a low polymerization degree according to a polymerization of the cyclic product by ring opening with a heat treatment at 100° C. to 300° C. in the presence of a clay-like solid catalyst (Japanese Unexamined Pat. Publication (Kokai) No. 54-93100). Also, by using the same cyclic product with a low polymerization degree as mentioned above, it has been proposed to produce a polysilazane with a high molecular weight according to a polymerization of the cyclic product by mixing it with bis(trimethylsilyl)amine and subjecting it to ring opening by heating at 110° C. in the presence of a ruthenium catalyst.

On the other hand, also known is a ladder-like polysilazane which is prepared by allowing an organodichlorosilane to react with dry ammonia, and then removing ammonium chloride to obtain a cyclic silazane with a low polymerization degree, followed by a further reaction with the use of a catalyst such as KH, NaH, etc., (D. Seyferth et al., Communication of the American Ceramic Society, C-132(6), 1984). The ladder-like polysilizane with a high molecular weight is represented by the following formula:

wherein $R^1$ is an alkyl group, an aryl group, etc., $R^2$ is hydrogen, an alkyl group, etc., and $0.37 \leq a \leq 0.41$, $0.02 \leq b \leq 0.04$, $0.57 \leq c \leq 0.60$, $a+b+c=1$.

The above cyclic polysilazane with a low molecular weight is not desirable as a ceramic starting material because it is susceptible to hydrolysis with water, etc., in the air, and the vaporization loss during firing at a high temperature is great. Further, the polysilazane is produced at a disadvantageously low yield.

Also, the high molecular weight polysilazane polymerized by ring opening the low molecular weight cyclic polysilazane is a firm polymer insoluble in organic solvents and, therefore, it is not desirable for utilization as a ceramic starting material, a densifying agent, a polymer hardening agent, or a surface treating agent.

The ladder-like polysilazane with a high molecular weight as mentioned above, although it is of interest as a ceramic starting material, requires a large number of steps and expensive catalysts or reaction terminators such as potassium hydride or methyl iodide (which cannot also be reused) in its preparation. Besides, since it is required to highly dry tetrahydrofuran used as the solvent, the production cost per unit weight of ceramics is disadvantageously high. Also, while it is indispensable to use a catalyst such as potassium hydride and a solvent such as dry tetrahydrofuran in its production, potassium hydride will react vigorously with water and will ignite if an organic solvent is co-present. On the other hand, dry tetrahydrofuran will be readily oxidized to form a highly explosive peroxide. Thus, these compounds are disadvantageous in that they can be handled only with extreme difficulty and with a low safety factor.

SUMMARY OF THE INVENTION

The object of the present invention is to obviate the above mentioned problems.

The present invention attains the above object by providing a polyorgano(hydro)silazane having the following compositional formula:

wherein R may be different and is selected from the group consisting of an alkyl group, an alkenyl group, a cycloalkyl group, an aryl group, a group other than these groups in which the atom directly bound to Si is carbon, an alkylsilyl group, an alkylamino group, and an alkoxy group, and $0.4 < x < 1$.

This polyorgano(hydro)silazane is a mixture of polymers having various structures, but it is considered that it consists basically of the linear portion as represented by the following formula (II) and the cyclic portion represented by the following formula (III), both ends of the linear portion being bound to the cyclic portions.

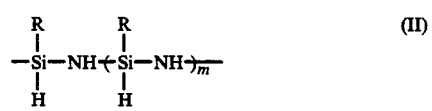

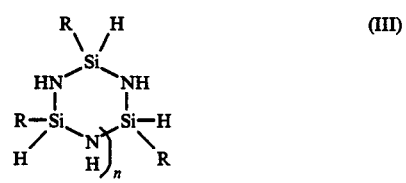

An example is shown by the following formula IV.

-continued

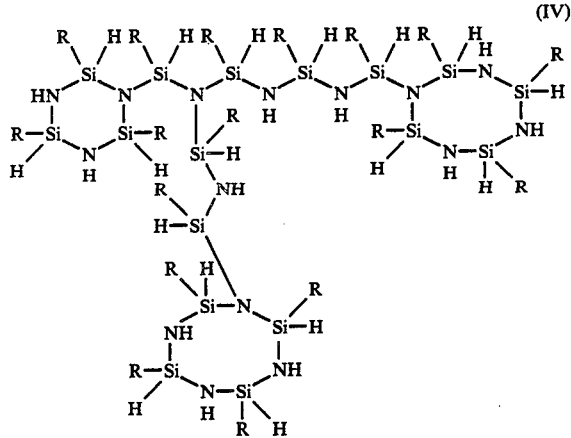

(IV)

Also, although all of the compounds are not enumerated, the compounds may be generalized as shown by the following formula (V).

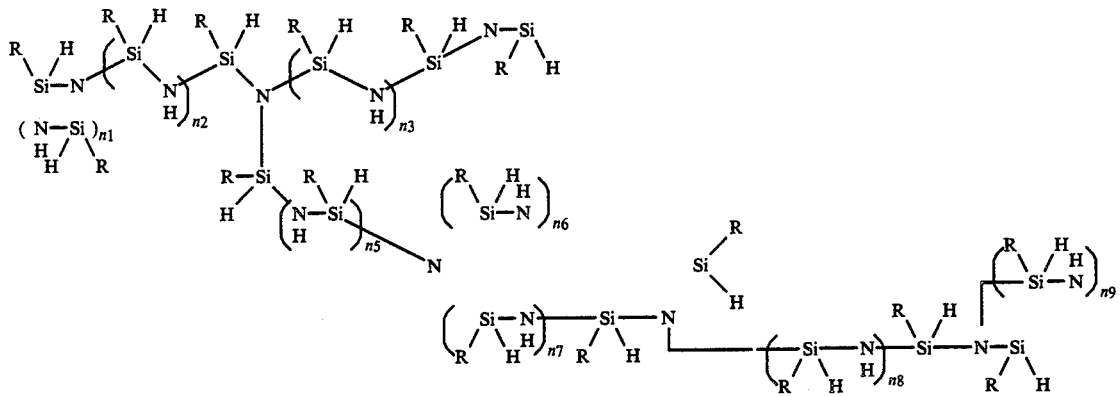

(V)

[$n_i$ (i = 1 to 9): integer]

Thus, generally speaking, in a whole structure in which the linear portion and the cyclic portion as shown by the above formulae (II) and (III) constituted of recurring units represented by the following formula (VI):

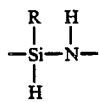

(VI)

are bound or branched in various forms, a part of those linear portions or cyclic portions contains additively the constituent portions represented by the formula (VII):

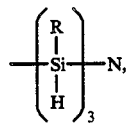

(VII)

thus providing a structure having the above composition $(RSiHNH)_x[(RSiH)_{1.5}N]_{1-x}$ as a whole.

The polymerization degree, calculated with (RSiHNH) as the recurring unit, of the polyorgano(hydro)silazane according to the present invention can be about 4 to 1700 or higher.

The organo group contained in the polyorgano(hydro)silazane according to the present invention may include, as mentioned above, an alkyl group, an alkenyl group, a cycloalkyl group, an aryl group, an alkylsilyl group, an alkylamino group, and an alkoxy group. General examples thereof may include alkyl groups having 1 to 7 carbon atoms, alkenyl groups having 2 to 7 carbon atoms, cycloalkyl groups having 5 to 7 carbon atoms, aryl groups such as phenyl, tolyl, xylyl, mesityl, cumenyl, benzyl, phenethyl, α-methylbenzyl, benzhydryl, trityl, styryl, cinnamyl, biphenylyl, naphthyl and the like, alkylsilyl groups having 1 to 7 carbon atoms, alkylamino groups having 1 to 7 carbon atoms, and alkoxy groups having 1 to 7 carbon atoms.

The polyorgano(hydro)silazane according to the present invention is novel in that it has a moiety represented by $(RSiH)_{1.5}N$ in the above compositional formula, and its existing amount is in a range as represented by $0.4 < x < 1$ in the above compositional formula.

The present invention also relates to a process for producing such a polyorgano(hydro)silazane, the process comprising the steps of: reacting organo(hydro)diholosilane with a base to form a complex thereof, followed by reacting the complex with dry ammonia to form a polyorgano(hydro)silazane having the following compositional formula (I):

$(RSiHNH)_x[(RSiH)_{1.5}N]_{1-x}$ wherein R may be different and is selected from the group consisting of an alkyl group, an alkenyl group, a cycloalkyl group, an aryl group, a group other than these groups in which the atom directly bound to Si is carbon, an alkylsylyl group, an alkylamino group, and an alkoxy group, and $0.4 < x \leq 1$.

The organo(hydro)dihalosilane to be used is represented by the formula (VIII):

(VIII)

wherein R is selected from the group consisting of an alkyl group, an alkenyl group, a cycloalkyl group, an aryl group, a group other than these groups in which the atom bonded directly to Si is carbon, an alkylsilyl group, an alkylamino group, and an alkoxy group, and X represents a halogen. Among them, R may be generally an alkyl group having 1 to 7, preferably 1 to 5, more preferably 1 to 2 carbon atoms, an alkenyl group having 2 to 7 carbon atoms, a cycloalkyl group having 5 to 7 carbon atoms, or an aryl group, and X may be generally fluorine, chlorine, bromine, or iodine, preferably chlorine. As the aryl group, there may be employed phenyl, tolyl, xylyl, mesithyl, cumenyl, benzyl, phenethyl, α-methylbenzyl, benzhydryl, trityl, styryl, cinnamyl, biphenylyl, naphthyl and the like. As the alkylsilyl group (mono, di, tri-substituted derivative), alkylamino group (mono, di-substituted derivative), and the alkoxy group, those having 1 to 7 carbon atoms may be generally used.

The usable base can be selected widely from among the bases capable of forming an adduct with a halosilane, particularly preferably, a Lewis base is used which will not undergo reactions other than the reaction of forming an adduct with a halosilane. Such bases may include, for example, tertiary amines (trialkylamines such as trimethylamine, dimethylethylamine, diethylmethylamine, triethylamine and the like, pyridine, picoline, dimethylaniline and derivatives of these), secondary amines having groups with steric hindrance, phosphine, stibine and arsine, and derivatives of these (e.g., trimethylphosphine, dimethylethylphosphine, methyldiethylphosphine, triethylphosphine, trimethylstibine, trimethylarsine, triethylarsine, etc.). Among them, a base having a low biling point and being less basic than ammonia (e.g., pyridine, picoline, trimethylphosphine, dimethylethylphosphine, methyldiethylphosphine, triethylphosphine) is preferred. Particularly, pyridine and picoline are preferred from the viewpoints of handling and economy.

The base to be used in the present invention is less expensive than the potassium hydride or methyliodide of the prior art, and can be reused, whereby the production cost becomes advantageously lower.

The amount of the Lewis base relative to the organo(hydro)dihalosilane may be 0.5 or higher in terms of molar ratio, preferably 1.0 or higher, more preferably 1.5 or higher.

In the present invention, a complex is formed by adding a Lewis base to the above organo(hydro)dihalosilane. During this reaction, as the reaction solvent, it is preferable to use a Lewis base alone or a mixture of a non-reactive solvent with a Lewis base. As the non-reactive solvent, it is possible to use hydrocarbon solvents such as aliphatic hydrocarbons, alicyclic hydrocarbons, and aromatic hydrocarbons, halogenated hydrocarbons such as halogenated methane, halogenated ethane, halogenated benzene, and the like, and ethers such as aliphatic ethers, alicyclic ethers, etc.

The preferable solvents are halogenated hydrocarbons such as methylene chloride, chloroform, carbon tetrachloride, bromoform, ethylenechloride, ethylidenechloride, trichloroethane, tetrachloroethane, and the like; ethers such as ethyl ether, isopropyl ether, ethyl butyl ether, butyl ether, dioxane, dimethyldioxane, tetrahydrofuran, tetrahydropyrane, and the like; and hydrocarbons such as pentane, hexane, isohexane, methylpentane, heptane, isoheptane, octane, isooctane, cyclopentane, methylcyclopentane, cyclohexane, methylcyclohexane, benzene, toluene, xylene, ethylbenzene, and the like. Of these solvents, dichloromethane and pyridine are particularly preferred, with respect to safety and other factors.

The concentration of the organo(hydro)dihalosilane in the solvent may be any desired concentration but is preferably within the range of from 1 to 15% by weight (hereinafter abbreviated as %). Also, as the conditions for forming the complex, the temperature may be within the range at which the reaction system can be a liquid, but is preferably a normal temperature, and the pressure may be preferably a normal pressure. Since the reaction is very rapid, the reaction time can be determined as desired.

Next, the complex thus produced is allowed to react with dry ammonia to carry out ammonolysis. The ammonia to be used in this reaction may be either gaseous or liquid. Drying of ammonia may be preferably carried out by, for example, passing it through solid sodium hydroxide, followed by passing it through metallic sodium. The amount of ammonia added may be 3.0 to 20-fold in terms of molar ratio relative to the organo(hydro)dihalosilane, preferably 4 to 15-fold, more preferably 5 to 10-fold. The reaction solvent, the reaction temperature, the reaction pressure, and the reaction time may be under the same conditions as used in the formation of the complex. However, in a closed system, the reaction is conducted under ammonia pressurization. Also, the water content in the reaction system may be desirably, for example, 500 ppm or less.

The polymerization degree of polyorgano(hydro)silazane can be increased by heating, and those having polymerization degrees with (RSiHNH) as the recurring unit, of about 4 to 1700 are generally available, and further, those with a higher polymerization degree also may be available.

After completion of the reaction, the polyorgano(hydro)silazane is separated by a conventional means such as centrifugation.

The novel polyorgano(hydro)silazane provided by the present invention is a ceramic starting material having high strength at high temperature with little reduction in weight by heating. Further, when it is used as a hardening agent for polyester resin or epoxy resin, tensile strength and thermal stability can be improved, while when it is used as the coating agent, abrasion resistance, water-proof workability and acid resistance can be improved.

Accordingly the polyorgano(hydro)silazane according to the present invention can be extremely widely used as the starting materials of silicon carbide nitrides, etc., hardening agents for various synthetic resins, coating agents, water repellents, stabilizers of silicone rubbers, and films, etc.

Also, the novel polyorgano(hydro)silazane has advantages such that it is soluble in solvents and is easy to handle, that it has a high in yield of the product, and that the production cost per unit weight of cermaics is low.

The process for producing the polyorgano(hydro)silazane according to the present invention has an advantage of enhanced safety during the process, in addition to the above-mentioned advantages of the product obtained by the process.

EXAMPLE

EXAMPLE 1 (ammonolysis of methyldichlorosilane complex)

A device equipped with a gas blowing pipe, a mechanical stirrer, a Dewar condenser and a dropping funnel on a four-necked flask having a 200 ml inner volume was used and the reaction system was replaced with nitrogen gas. The device was cooled in an ice-bath, and 6.00 g of methyldichlorosilane (CH$_3$SiHCl$_2$) (52.2 mmol) and 70 ml of dry dichloromethane were charged thereinto. Next, 16.6 g (210 mmol) of dry pyridine was added dropwise through the dropping funnel to form a complex, and a colorless solution was obtained. Then, while stirring the solution, 4.10 g (240 mmol) of dry ammonia and nitrogen gas were blown therein to carry out ammonolysis. During the reaction, a small amount of fumes was generated, but there no trouble occurred such as a clogging of the gas pathway or sticking or deposition on the inner wall of the reactor. The addition of ammonia caused the reaction mixture to become a white slurry. After completion of the reaction, the reaction mixture was subjected to centrifugation, followed by filtration. The solvent was removed under reduced pressure from the filtrate to give 2.80 g of polymethyl(hydro)silazane as a colorless viscous oil. The yield was 90.7% based on Si.

The average molecular weight of the viscous oil was measured by the cryoscopic method (solvent: benzene) and was found to be 1090.

Figure 1:
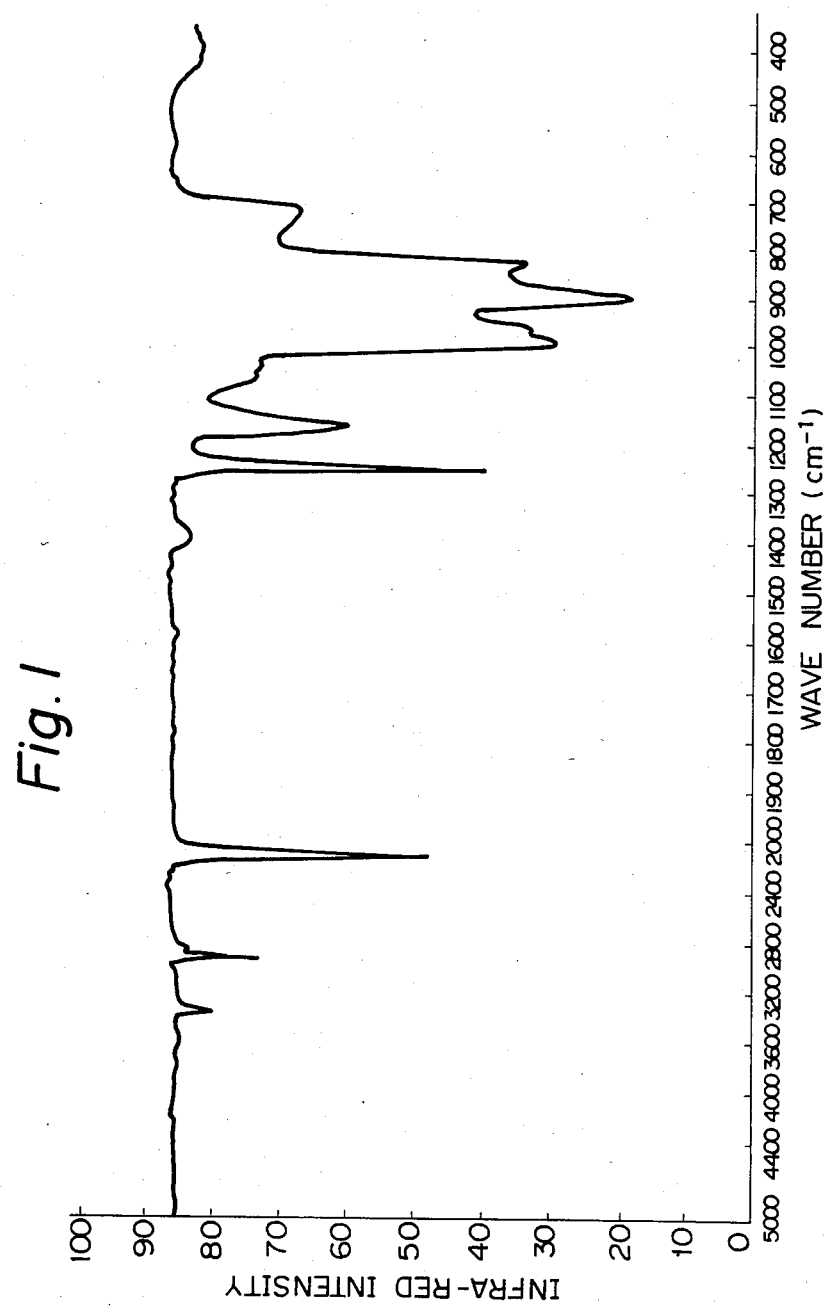
FIG. 1 is an IR (infrared absorption) sectrum of the product in Example 1.

The IR (infrared absorption) spectrum (solvent CHCl$_3$) exhibits absorptions based on NH at the wave numbers (cm$^{-1}$) 3380 and 1170; absorption based on CH$_3$ at 2960; absorption based on SiH at 2130; absorption based on SiCH$_3$ at 1260; and absorptions based on SiH and SiNSi at 1020–880, as shown in FIG. 1.

Figure 2:
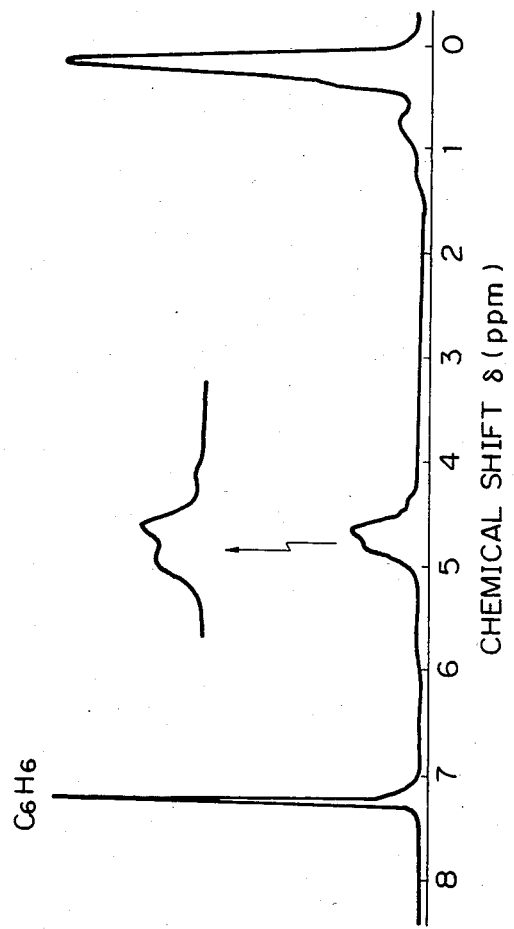
FIG. 2 is a $^1$H NMR (proton neucler magnetic resonance) spectrum of the product in Example 1.

On the other hand, all of the $^1$H NMR (protone nuclear magnetic resonance) (60 MHz, solvent CDCl$_3$/standard substance C$_6$H$_6$) show broad absorptions as shown in FIG. 2. That is, δ0.2 (br, 3H SiCH$_3$); 0.8 (br, 0.84H, NH); 4.7 and 4.8 (br, 1H SiH).

The $^1$H NMR date is different from that of the product according to the prior art method shown in Examples 2 and 4 (comparatives) and, therefore, the polymethyl(hydro)silazane according to the present invention was confirmed to be a novel compound.

The results of elemental analysis of the polymethyl(hydro)silazane of the present invention were, by weight %, Si: 46.7; C: 20.82; H: 8.42; N: 22.23.

From the above IR spectrum, $^1$H NMR spectrum, and the results of elemental analysis, the product was confirmed to be a novel compound having a composition of (CH$_3$SiHNH)$_{0.89}$(CH$_3$SiH)$_{1.5}$N$_{0.11}$.

The product was fired by a thermogravimetric analyzer in a nitrogen stream under the conditions of a temperature elevation speed of 5° C./min and a maximum reaching temperature of 1000° C. The weight of the black solid residue after firing was 44% of that before firing. Thus, it can be understood that the polysilazane produced according to the process of the present invention is highly economical as the starting material of a ceramic material.

Example 2 (ammonolysis of methyldichlorosilane; comparative)

The reaction was carried out in the same manner as Example 1 by using 24.3 g (0.211 mol) of methyldichlorosilane and 300 ml of dry dichloromethane and 18.1 g (1.06 mol) of dry ammonia without using dry pyridine, and 8.81 g of the reaction product was obtained as a colorless liquid. The yield was 70.7% based on Si, but the average molecular weight of this product was as low as 314, with the average polymerization degree being 5.3.

Also, the $^1$H NMR data is clearly different from that of the product in Example 1, as shown below.

δ(CDCl$_3$/C$_6$H$_6$), 0.2(br, 3H, SiCH$_3$), 0.9(br, 1H NH), 4.7 br, 1H SiH).

The polymethyl(hydro)silazane obtained here was fired by a thermogravimetric analyzer under the same conditions as in Example 1. The weight of the black solid residue after firing was 14% of that before firing.

Example 3 (ammonolysis of methyldichlorosilane complex)

The same device as used in Example 1 was employed. The four-necked flask was charged with 100 ml of dry pyridine, and this was ice-cooled. Next, 5.94 g (51.6 mmol) of methyldichlorosilane was added dropwise into the dry pyridine to obtain a colorless solution. The reaction mixture was ice-cooled, and ammonolysis was carried out by blowing 4.10 g (240 mmol) of dry ammonia together with nitrogen gas, under vigorous stirring, therein. The reaction mixture in the form of a white slurry was heated under reflux. The reaction mixture obtained was treated in the same manner as in Example 1 to obtain 2.65 g of polymethyl(hydro)silazane as a colorless viscous oil. The yield was 86.8% based on Si, and the average molecular weight was 1800. The product was confirmed by $^1$H NMR spectrum to have a composition of (CH$_3$SiHNH)$_{0.80}$[(CH$_3$SiH)$_{1.5}$N]$_{0.20}$.

Example 4 (conversion of the product of Example 2 to a high molecular weight compound in the presence of potassium hydride catalyst): comparative)

A four-necked flask having a 100 ml inner volume was equipped with a gas introducing pipe, a thermometer, a condenser and a dropping funnel, and a reaction system was replaced internally with argon gas. The four-necked flask was charged with 12 ml of dry tetrahydrofurane and 0.189 g (4.71 mmol) of potassium hydride, and magnetic stirring was initiated. In the dropping funnel, 5.06 g (85.6 mmol, based on (CH$_3$SiHNH) unit) of the synthetic product of Example 2 and 50 ml of dry tetrahydrofuran were charged, and they were added dropwise into potassium hydride. Hydrogen gas was generated gently. After the reaction at a room temperature overnight, a slightly yellow solution was obtained. Subsequently, 1.60 g (11.3 mmol) of methyl iodide and 1 ml of dry tetrahydrofuran were charged into the dropping funnel, and these were added dropwise into the reaction mixture, whereby a slightly yellow suspension was obtained. The solvent in the reaction mixture was evaporated under reduced pressure, the residue was centrifuged with the addition of 40 ml of dry n-hexane, followed by filtration. The solvent of the filtrate was evaporated under reduced pressure to give 4.91 g of polymethyl(hydro)silazane as a white powder (yield 97.0 wt. %). The product was found to have an average molecular weight of 1860. The $^1$H NMR data is clearly different from the product of Example 1, as shown below.

δ(CDCl$_3$/C$_6$H$_6$), 0.2(br, 3H, SiCH$_3$), 0.8(br, 0.44H, NH), 2.5(br, 0.10H, NCH$_3$), 4.7(br, 0.42H, SiH).

Also, the elemental analysis results of the polymethyl(hydro)silazane obtained here were (by wt %) C: 21.60%; H: 6.86; N: 22.55.

From the above $^1$H NMR data and the results of elemental analysis, the product was confirmed to have the following composition:

$$(-\underset{\underset{H}{|}}{\overset{\overset{CH_3}{|}}{Si}}-\underset{}{\overset{\overset{N}{|}}{N}}-)_{0.39} \quad (-\underset{\underset{H}{|}}{\overset{\overset{CH_3}{|}}{Si}}-\overset{\overset{CH_3}{|}}{N}-)_{0.03} \quad (-\underset{|}{\overset{\overset{CH_3}{|}}{Si}}-\underset{|}{N}-)_{0.58}$$

This was fired by a thermogravimetric analyzer under the same conditions as used in Example 1. The weight of the black solid residue after firing was 84% of that before firing.

Example 5 (ammonolysis of a reaction mixture of phenyldichlorosilane and pyridine)

When the reaction was carried out in the same manner as in Example 1 by using 4.12 g (23.3 mmol) of phenyldichlorosilane (C$_6$H$_5$SiHCl$_2$), 7.43 g (93.9 mmol) of dry pyridine, 3.40 g (200 mmol) of dry ammonia, and 100 ml of dry dichloromethane, 2.82 g of a polyphenyl(hydro)silazane was obtained as a colorless highly viscous oil. The yield was 100% based on Si and the average molecular weight 499.

Figure 3:
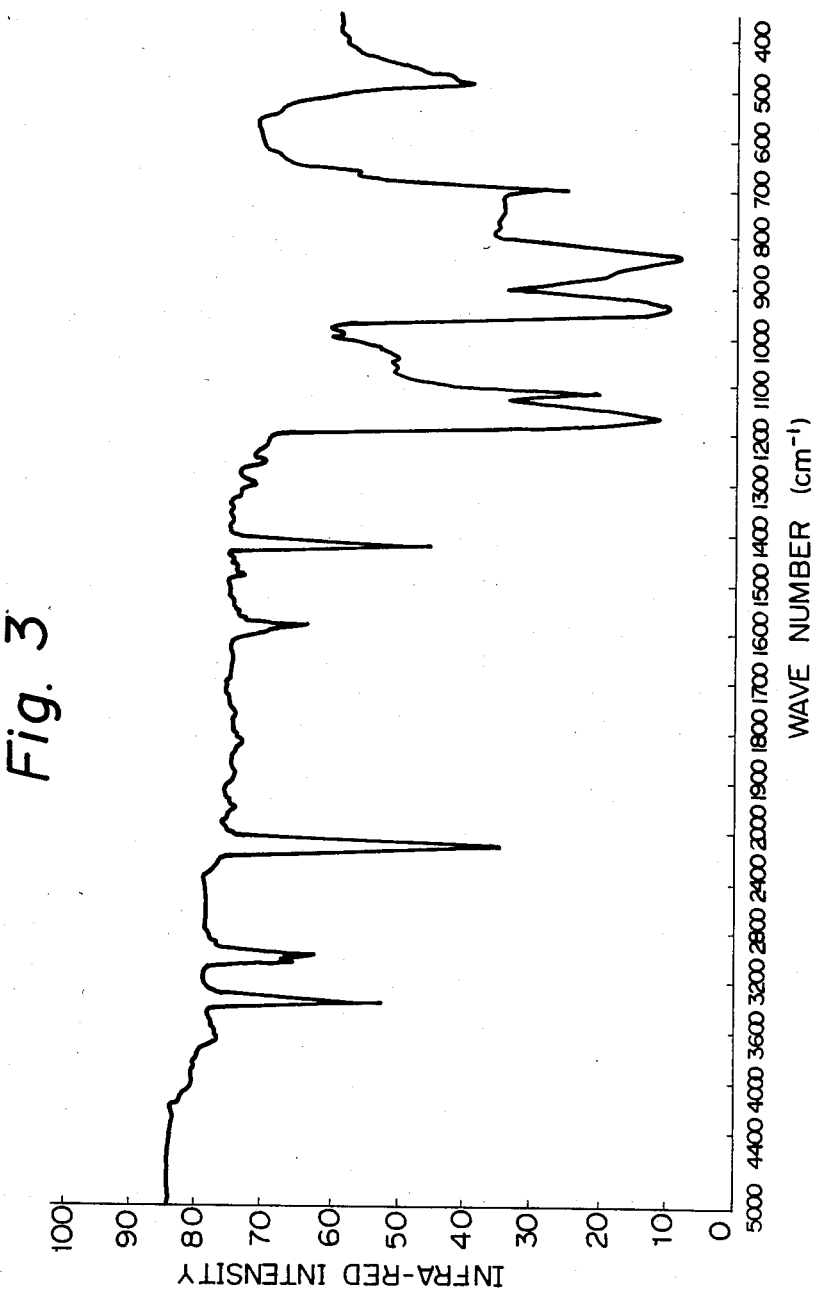
FIG. 3 is an IR spectrum of the product in Example 5.

The IR spectrum (CHCl$_3$) exhibits absorptions based on NH at wave numbers (cm$^{-1}$) 3400 and 1170; absorptions based on phenyl group at 3060, 3010, 1590 and 1430; absorption based on SiH at 2130; absorptions based on SiH and SiNSi at 980–800, as shown FIG. 3.

Figure 4:
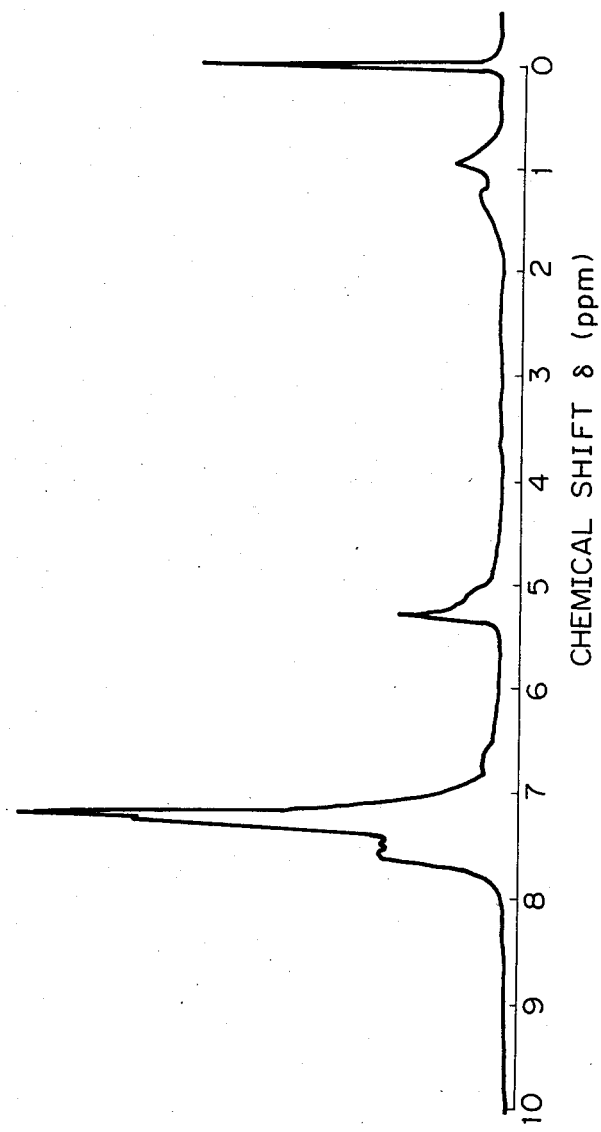
FIG. 4 is a $^1$H NMR spectrum of the product in Example 5.

The $^1$H NMR spectrum (60 MHz, DCDl$_3$/TMS) shows all broad absorptions, as shown in FIG. 4. That is, δ0.5–1.9(br, 0.9H, NH); 4.7–5.5(br, 1H, SiH); 6.4–8.0(br, 5H, C$_6$H$_5$). This spectrum is slightly different from the spectrum of the product in Example 6, in the integral ratio of the absorption based on NH. Also, the results of elemental analysis of the polyphenyl(hydro)silazane of the present invention were (by wt %) Si: 22.5; C: 60.74; H: 5.88; N: 10.88.

From the above IR spectrum, $^1$H NMR spectrum, and the results of elemental analysis, the product was confirmed to be a novel compound having a composition of (PhSiHNH)$_{0.93}$[(PhSiH)$_{1.5}$N]$_{0.07}$. Also, when the product was fired under the same conditions as in Example 1, a black solid was obtained at a yield of 52%.

Example 6 (ammonolysis of phenyldichlorosilane; comparative)

The same reaction as in Example 5 was carried out by using 4.12 g (23.3 mmol) of phenyldichlorosilane, 100 ml of dry dichloromethane, and 3.30 g (194 mmol) of dry ammonia, without using dry pyridine, to obtain 2.71 g of a product as a colorless viscous oil. The yield was 96.0% based on Si and the average molecular weight 424.

The $^1$H NMR data was as shown below.

δ(CDCl$_3$/TMS)0.6–1.9(br, 1H, NH); 4.7–5.5(br, 1H, SiH); 6.6–8.0(br, 5H, C$_6$H$_5$).

When this product was fired under the same conditions as in Example 1, a black solid was obtained at a yield of 44%.

I claim:

1. A polyorgano(hydro)silazane represented by the following compositional formula (I):

$$(RSiHNH)_x[(RSiH)_{1.5}N]_{1-x} \qquad (I)$$

wherein R may be different and is selected from the group consisting of an alkyl group, an alkenyl group, a cycloalkyl group, an aryl group, a group other than these groups in which the atom directly bound to Si is carbon, an alkylsilyl group, an alkylamino group, and an alkoxy group, and $0.4 < x < 1$.

2. A polyorgano(hydro)silazane according to claim 1, wherein said polyorgano(hydro)silazane has a structure comprising a linear portion as represented by the following formula (II) and a cyclic portion represented by the following formula (III), the ends of the linear portion being bound to the cyclic portions.

$$-\underset{\underset{H}{|}}{\overset{\overset{R}{|}}{Si}}-NH\left(\underset{\underset{H}{|}}{\overset{\overset{R}{|}}{Si}}-NH\right)_{\!m}- \qquad (II)$$

$$\begin{pmatrix} R\diagdown\phantom{xx}/H \\ \phantom{xx}Si \\ HN\diagup\phantom{xx}\diagdown NH \\ R-\underset{H}{Si}\phantom{xxxxx}\underset{R}{Si}-H \\ \diagdown N\diagup \\ \phantom{xxx}H \end{pmatrix}_{\!n} \qquad (III)$$

wherein m and n are an integer, respectively.

3. A polyorgano(hydro)silazane according to claim 2, wherein said linear portion or said cyclic portion has a branch comprising another linear portion represented by said formula (IV).

$$\left(\begin{matrix} R \\ | \\ -Si- \\ | \\ N \end{matrix}\right)_{\!3} N \qquad (IV)$$

4. A polyorgano(hydro)silazane according to claim 1, wherein the polymerization degree, calculated by (RSiHNH) as the recurring unit, of the polyorgano(hydro)silazane is from 4 to 1700.

5. A polyorgano(hydro)silazane according to claim 1, wherein the R in said formula (I) may be different and is selected from the group consisting of alkyl groups having 1 to 7 carbon atoms, alkenyl groups having 2 to 7 carbon atoms, cycloalkyl group having 5 to 7 carbon atoms, aryl groups, alkylsilyl groups having 1 to 7 carbon atoms, alkylamino groups having 1 to 7 carbon atoms, and alkoxy groups having 1 to 7 carbon atoms.

6. A polyorgano(hydro)silazane according to claim 5, wherein the R in said formula (I) may be different and is selected from the group consisting of methyl, ethyle, n-propyl, i-propyl, vinyl, alkyl, benzyl, phenyl and tolyl.

7. A process for producing a polyorgano(hydro)silazane, comprising the steps of: reacting an organo(hydro)dihalosilane with a base to form a complex thereof, and then reacting the complex with dry ammonia to form a polyorgano(hydro)silazane having the following compositional formula:

$$(RSiHNH)_x[(RSiH)_{1.5}N]_{1-x}$$

wherein R may be different and is selected from the group consisting of an alkyl group, an alkenyl group, a cycloalkyl group, an aryl group, a group other than these groups in which the atom directly bound to Si is carbon, an alkylsilyl group, an alkylamino group, and an alkoxy group, and $0.4 < x > 1$.

8. A process according to claim 7, wherein said organo(hydro)dihalosilane has a formula (V):

$$R-\underset{\underset{H}{|}}{\overset{\overset{X}{|}}{Si}}-X \qquad (V)$$

wherein R may be different and is selected from the group consisting of an alkyl group, an alkenyl group, a cycloalkyl group, an aryl group, a group other than said groups in which the atom bound directly to Si is carbon, an alkylsilyl group, an alkylamino group, and an alkoxy group, and X is a halogen.

9. A process according to claim 7, wherein the R in said formula (V) may be different and is selected from the group consisting of an alkyl group having 1 to 7 carbon atoms, an alkenyl group having 2 to 7 carbon atoms, a cycloalkyl group having 5 to 7 carbon atoms, an aryl group, an alkylsilyl group having 1 to 7 carbon atoms, an alkylamino group having 1 to 7 carbon atoms, and an alkoxy group having 1 to 7 carbon atoms.

10. A process according to claim 9, wherein the R in said formula (V) may be different and is selected from the group consisting of methyl, ethylene, n-propyl, i-propyl, vinyl, alkyl, benzyl, phenyl and tolyl.

11. A process according to claim 7, wherein said base is a Lewis base.

12. A process according to claim 11, wherein said Lewis base is selected from the group consisting of tertiary amines and secondary amines having groups with a steric hindrance, phosphine, stibine, arsine, and their derivatives.

13. A process according to claim 12, wherein said Lewis base is selected from the group consisting of pyridine, picoline, trimethylphosphine, dimethylethylphosphine, methyldiethylphosphine, and triethylphosphine.

14. A process according to claim 7, wherein the mole ratio of the base to be organo(hydro)dihalosilane is 0.5 or higher.

15. A process according to claim 14, wherein said mole ratio of the base to the organo(hydro)dihalosilane is 1.5 or higher.

16. A process according to claim 7, wherein said reaction of the organo(hydro)dihalosilane with the base to form a complex thereof is conducted in said base alone as a reaction solvent.

17. A process according to claim 7, wherein said reaction of the organo(hydro)dihalosilane with the base to form a complex is conducted in a mixture of said base and a non-reactive solvent as a reaction solvent.

18. A process according to claim 17, wherein said non-reactive solvent is selected from the group consisting of aliphatic hydrocarbons, alicyclic hydrocarbons, aromatic hydrocarbons, halogenated hydrocarbons and ethers, and a mixture thereof.

19. A process according to claim 7, wherein the mole ratio of the dry ammonia to the organo(hydro)dihalosilane is from 3.0 to 20.

* * * * *

UNITED STATES PATENT AND TRADEMARK OFFICE
CERTIFICATE OF CORRECTION

PATENT NO. : 4,659,850

DATED : April 21, 1987

INVENTOR(S) Mikiro Arai et al.

It is certified that error appears in the above-identified patent and that said Letters Patent are hereby corrected as shown below:

column 1, line 22, amend " -RSiHNH) "

to read --   —(-RSiHNH-)—   -- column 2, formula III, amend to read

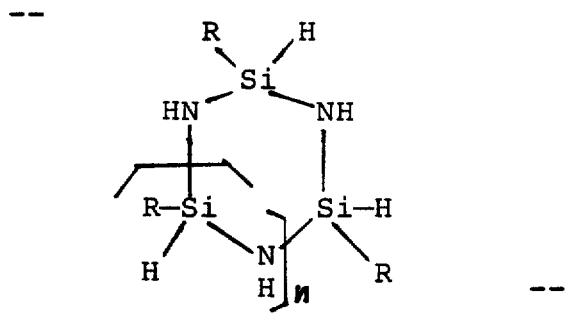

columns 3 and 4, formula V, amend to read

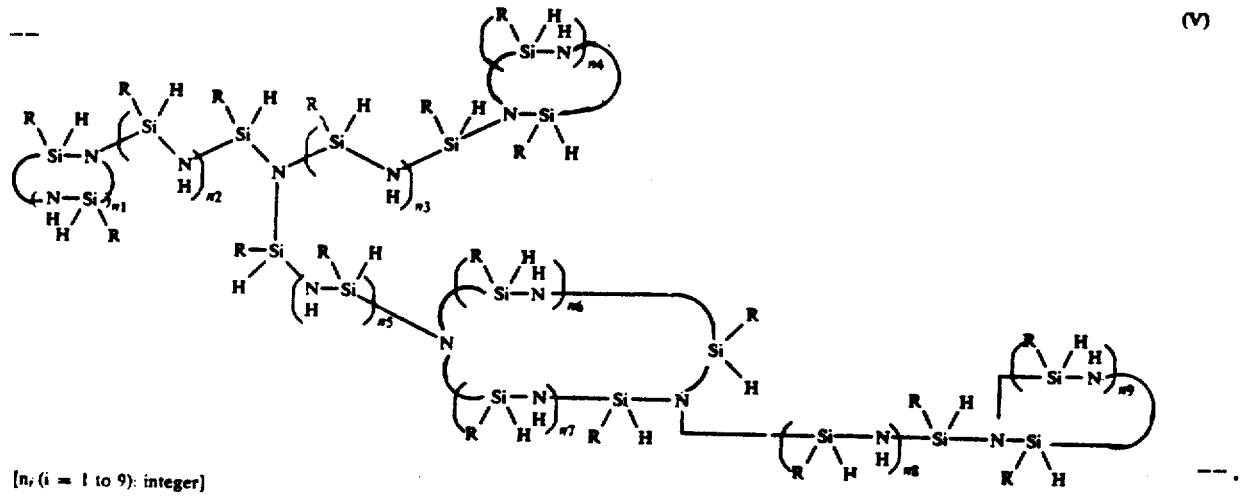

[$n_i$ (i = 1 to 9): integer]   --.

UNITED STATES PATENT AND TRADEMARK OFFICE
CERTIFICATE OF CORRECTION

PATENT NO. : 4,659,850
DATED : April 21, 1987
INVENTOR(S) : Mikiro Arai et al.

It is certified that error appears in the above-identified patent and that said Letters Patent are hereby corrected as shown below:

Column 5, line 34, amend "biling" to read --boiling--
Column 9, line 40, amend "DCDl$_3$/TMS" to read --CDCl$_3$/TMS--
Claim 2, formula III
    amend to read

--

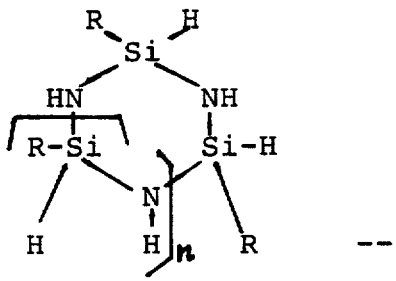

-- claim 6, line 3, amend "ethyle" to read --ethyl--
claim 7, last line, amend "0.4<x>1" to read --0.4<x≤1--
claim 8, line 2, amend "(V)" to read --(VIII)--
    line 3, amend "(V)" to read --(VIII)--
claim 9, line 2, amend "(V)" to read --(VIII)--
claim 10, line 2, amend "(V)" to read --(VIII)--

UNITED STATES PATENT AND TRADEMARK OFFICE
CERTIFICATE OF CORRECTION

PATENT NO. : 4,659,850

DATED : April 21, 1987

INVENTOR(S) : Mikiro Arai et al.

It is certified that error appears in the above-identified patent and that said Letters Patent is hereby corrected as shown below:

Claim 10, line 2, amend "(V)" to read -- (VIII) --.

Signed and Sealed this

Fourteenth Day of March, 1989

Attest:

DONALD J. QUIGG

*Attesting Officer*  *Commissioner of Patents and Trademarks*